(12) United States Patent
Menon-Johansson

(10) Patent No.: US 10,203,340 B2
(45) Date of Patent: Feb. 12, 2019

(54) PREGNANCY TESTING

(71) Applicants: Anatole Sebastian Menon-Johansson, Hounslow Middlesex (GB); GUY'S AND ST. THOMAS'S NHS FOUNDATION TRUST, London (GB)

(72) Inventor: Anatole Sebastian Menon-Johansson, Hounslow Middlesex (GB)

(73) Assignees: Anatole Sebastian Menon-Johansson, Hounslow Middlesex (GB); Guy's and St. Thomas's NHS Foundation Trust, London (GB)

( * ) Notice: Subject to any disclaimer, the term of this patent is extended or adjusted under 35 U.S.C. 154(b) by 0 days.

(21) Appl. No.: 14/201,601

(22) Filed: Mar. 7, 2014

(65) Prior Publication Data
US 2014/0273028 A1    Sep. 18, 2014

Related U.S. Application Data

(63) Continuation of application No. 13/129,732, filed as application No. PCT/GB2009/051548 on Nov. 16, 2009, now abandoned.

(30) Foreign Application Priority Data

Nov. 17, 2008    (GB) .................................. 0820999.1

(51) Int. Cl.
*G01N 33/68* (2006.01)
*G01N 33/74* (2006.01)

(52) U.S. Cl.
CPC ........... *G01N 33/689* (2013.01); *G01N 33/74* (2013.01); *G01N 2333/5752* (2013.01); *G01N 2333/59* (2013.01)

(58) Field of Classification Search
CPC ....... G01N 2333/5752; G01N 2333/59; G01N 33/689; G01N 33/74; Y10S 436/814; Y10S 436/818
See application file for complete search history.

(56) References Cited

U.S. PATENT DOCUMENTS

| | | | |
|---|---|---|---|
| 3,892,841 A | 7/1975 | Barg | |
| 5,504,013 A | 4/1996 | Senior | |
| 6,156,271 A * | 12/2000 | May | 422/412 |
| 7,235,359 B2 | 6/2007 | Lo et al. | |
| 2002/0123671 A1 | 9/2002 | Haaland | |
| 2005/0037511 A1 * | 2/2005 | Sharrock | 436/164 |
| 2008/0213875 A1 | 9/2008 | Sharrock et al. | |

FOREIGN PATENT DOCUMENTS

| | | | | |
|---|---|---|---|---|
| EP | 0291194 A1 | 11/1988 | | |
| GB | 1597266 A | 9/1981 | | |
| WO | 95/13542 A1 | 5/1995 | | |
| WO | 96/09546 A1 | 3/1996 | | |
| WO | WO 03/062824 | * | 7/2003 | ........... G01N 33/543 |
| WO | 04/065629 A1 | 8/2004 | | |
| WO | 06/100415 A1 | 9/2006 | | |
| WO | 2007/017648 A1 | 2/2007 | | |
| WO | WO 2009097579 | * | 8/2009 | ............. G01N 33/68 |

OTHER PUBLICATIONS

Biswas et al., (J. Endocr. 1972, vol. 54, pp. 251-261).*
Technical note Abcam (1998;Mouse anti-human placental lactogen clone INN-hPL-37 retrieved from http://www.abcam.com/human-placental-lactogen-epitope-2-antibody-inn-hpl-37-ab11396.html on Jan. 8, 2017).*
Fiorella et al., "Papanicolaou Smears in Pregnancy. Positivity of Exfoliated Cells for Human Chorionic Gonadotropin and Human Placental Lactogen", Acta Cytol., 37(4):451-456 (1993).
Josimovich et al., "Human placental lactogen (HPL), a trophoblastic hormone synergizing with chorionic gonadotropin and potentiating the anabolic effects of pituitary growth hormone", Am. J. Obst. Gynec., 88(7):867-879 (1964).
Kaplan et al., "Immunoassay for Human Chorionic 'Growth Hormone-Prolactin' in Serum and Urine", Science 147, (3659):751-753 (1965).
Sorensen et al., "Differential increase in the maternal serum concentrations of the placental proteins human chorionic gonadotrophin, pregnancy-specific beta 1-glycoprotein, human placental lactogen and pregnancy-associated plasma protein-A during the first half of normal pregnancy, elucidated by means of a mathematical model", Hum. Reprod., 10(2):453-458 (1995).
Biswas et al., Human Chrorionic Somato-Mammotrophin in Serum and Urine in various stages of pregnancy: Its correlation with enzymes and oestrogens, Institute of Obstetrics and Gynaecology, Chelsea Hospital for Women, London, Dec. 4, 1971.
Moserr J., "Radioimmuninoassay of human Chrorionic Somatomam-motropin in Seum, amniotic fluid, and urine", Clinical Chemistry, 19(6) (1973).
Bersinger et al., "Maternal serum levels of placental proteins after in vitro fertilisation and ther implications for prenatal screening" Prenatal Diagnosis 24(6): 471-477 (2004).
Petersen et al., "Variations in serum relaxing (HRLX-2) concentration during human pregnancy" Acta Obstetrici and Gynecologica Scandinavica, Munksgaard, Copenhagen, DK, 74:251-256 (1995).
Furuhashi et al., "Retrograde time-scale analysis of humen placental lactogen beta human chronocic gonadotropin and unconjugated estriol levels in human maternal serum from the onset of spoantaneous labor", Gynecologig and obstetric Investigation, 18(5):264-268 (1984).

(Continued)

*Primary Examiner* — Tracy Vivlemore
*Assistant Examiner* — Carmencita M Belei
(74) *Attorney, Agent, or Firm* — Saul Ewing Arnstein & Lehr LLP; Debora Plehn-Dujowich

(57) ABSTRACT

A method of determining the stage (gestation) of a pregnancy—comprising the steps of quantifying the amount of the hormone hPL or a fragment thereof in a body fluid sample derived from a human female selected from a blood, plasma, serum and/or urine sample, and establishing the stage of pregnancy corresponding thereto. The disclosure also extends to a device adapted to detect the levels/amount of hPL or a fragment thereof in a body fluid sample, derived from a human female, selected from a blood, plasma, serum and/or urine sample, for establishing the stage of pregnancy.

8 Claims, 5 Drawing Sheets
Specification includes a Sequence Listing.

(56) References Cited

OTHER PUBLICATIONS

Christensen et al., "Hormones and enzymes Assays in Pregnancy" Acta Endocrinol, 76:201-208(1974).
Josimovich et al., "Placental Protein Hormones" Clin. Obs. Gynecol., 16:46-55 (1973).
Peeters et al., "Serum levels of human placental lactogen and human chrorionic gonadotropin in early pregnancy a maturational index of the placenta" American Jounral of Obstretica and Gynecology, 126(6): 707-711, (1976).
Whittaker et al., "A propective study to comapre serum human placental lactogen and menstrual dates for determining gestational age" American Journal of Obstetrics and Gynecology, 156(1):178-182, (1987).
Whittaker et al., "Accurate of Early Gestational Age in Normal and diabetic women by serum human placental lactogen concentration" Lancet, 2(8345);304-306 (1983).
DRG HPL ELISA Application Note (Sep. 2008, retrieved from URL diameb.ua/manuals/eng/1283G.PDF).
Appendix to U.S. Appl. No. 61/024,865, Jan. 30, 2008.

* cited by examiner

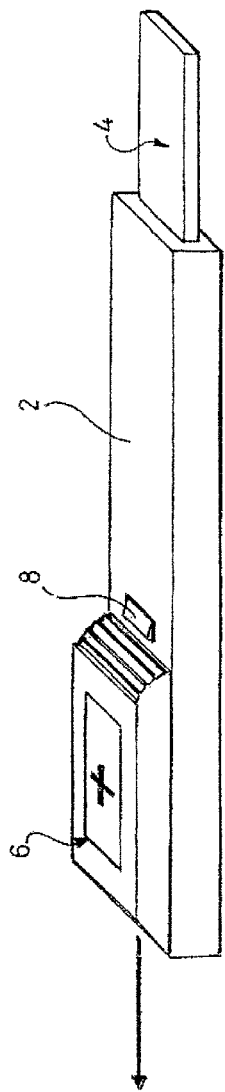
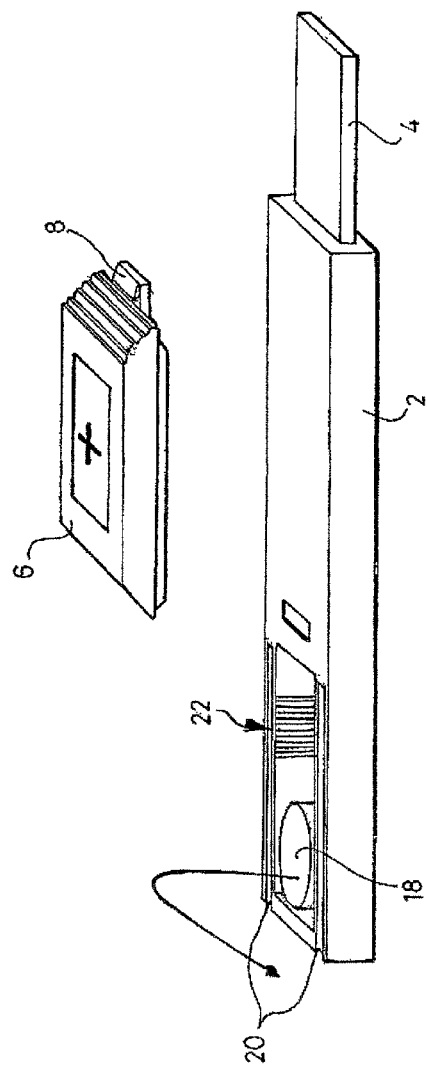

PREGNANCY TESTING

CROSS REFERENCE TO RELATED APPLICATIONS

This application is a Continuation of U.S. application Ser. No. 13/129,732 filed Jul. 13, 2011 (now abandoned), which is a 371 National Stage Application of International Application No. PCT/GB2009/051548 filed on Nov. 16, 2009, which designates the United States, and which claims the benefit of foreign priority under 35 U.S.C. § 119 of United Kingdom Application No. 0820999.1 filed Nov. 17, 2008, the contents of each are incorporated herein in their entirety by reference.

SEQUENCE LISTING

The instant application contains a Sequence Listing which has been submitted in ASCII format via EFS-Web and is hereby incorporated by reference in its entirety. Said ASCII copy, created on Mar. 7, 2014, is named 13129,732 and is 1,023,372 bytes in size.

DESCRIPTION

The disclosure relates to a method and device for establishing the approximate stage (gestation) of pregnancy of a human female, based on establishing the concentration of human placental lactogen (hPL) or a relevant fragment thereof in a body fluid sample from said female. The disclosure also relates to use of an anti-hPL antibody for identifying the stage of pregnancy.

Pregnancy tests are widely used by healthcare professionals and private individuals. Pregnancy tests have been available at supermarkets and pharmacies for a number of years. One of the most famous brands is CLEARBLUE®. The latter tests are provided as simple, robust devices (see for example EP 0291194) that can readily be used at home by individuals and a result is given in a matter of minutes. The tests are based on detecting the presence or absence of a hormone human chorionic gonadotrophin (hCG) in urine from the relevant female.

Traditionally the result of the test was positive or negative, i.e. pregnant or not pregnant. However, recently a more sophisticated test has been launched where the concentration of hCG is used to establish if the individual is 1-2, 2-3 or 3/3+ weeks pregnant. This test is described in published application WO 2006/100415.

Whilst this new test is useful, the information provided if the term of pregnancy is over three weeks is very limited. That is to say it simply indicates that the term of the pregnancy is 3 weeks or more.

If the stage of the pregnancy cannot be calculated from the information the pregnant woman herself can provide, for example because of incomplete or inaccurate information, the only other way to date the pregnancy, at the present time, is an ultrasound scan. Whilst the accuracy of ultrasound scans for determining the stage of the pregnancy is generally very high, and may be accurate within 3 or 4 days, this accuracy may be reduced for scans performed before week 13 of the pregnancy. Furthermore, it is not feasible to routinely determine the stage of a pregnancy using an ultrasound scan because of the resource implications and burden on the health care system. At the present time given the very high demand for scans, the first ultrasound scan is given at about 13 weeks, unless complications in the pregnancy are suspected.

It would be very useful to be in a position to date a pregnancy without recourse to an ultrasound scan, preferably using a simple non-invasive test.

The present inventor has found that the stage of a pregnancy can be correlated to the concentration of a hormone human placental lactogen.

The hormone itself has been known for a number of years and has been proposed as a biomarker for abnormalities in the pregnancy and/or foetus such as pre-eclampsia and fetal chromosomal aneuploidy amongst other things, see for example U.S. Pat. No. 7,235,359.

However, as far as we are aware it has never been proposed as useful for determining the stage of a normal pregnancy.

Thus in one aspect there is provided a method of determining the stage of a pregnancy comprising the steps of quantifying the concentration of hPL in a body fluid sample derived from a human female selected from a blood, plasma, serum and/or urine sample, and establishing the stage of pregnancy corresponding thereto.

hPL is also known as chorionic somatomammotropin hormone 1 or choriomammotropin lactogen. UniProt indicates that the peptide is 217 amino acids in length, as shown in SEQ ID NO: 1, but it also seems to exist in a 190 or 191 amino acids length form. The hormone has two subunits.

BRIEF DESCRIPTION OF THE DRAWINGS

FIGS. 3A and 3B show closed and open perspective views respectively of a device with a digital display unit.

Figure 1:
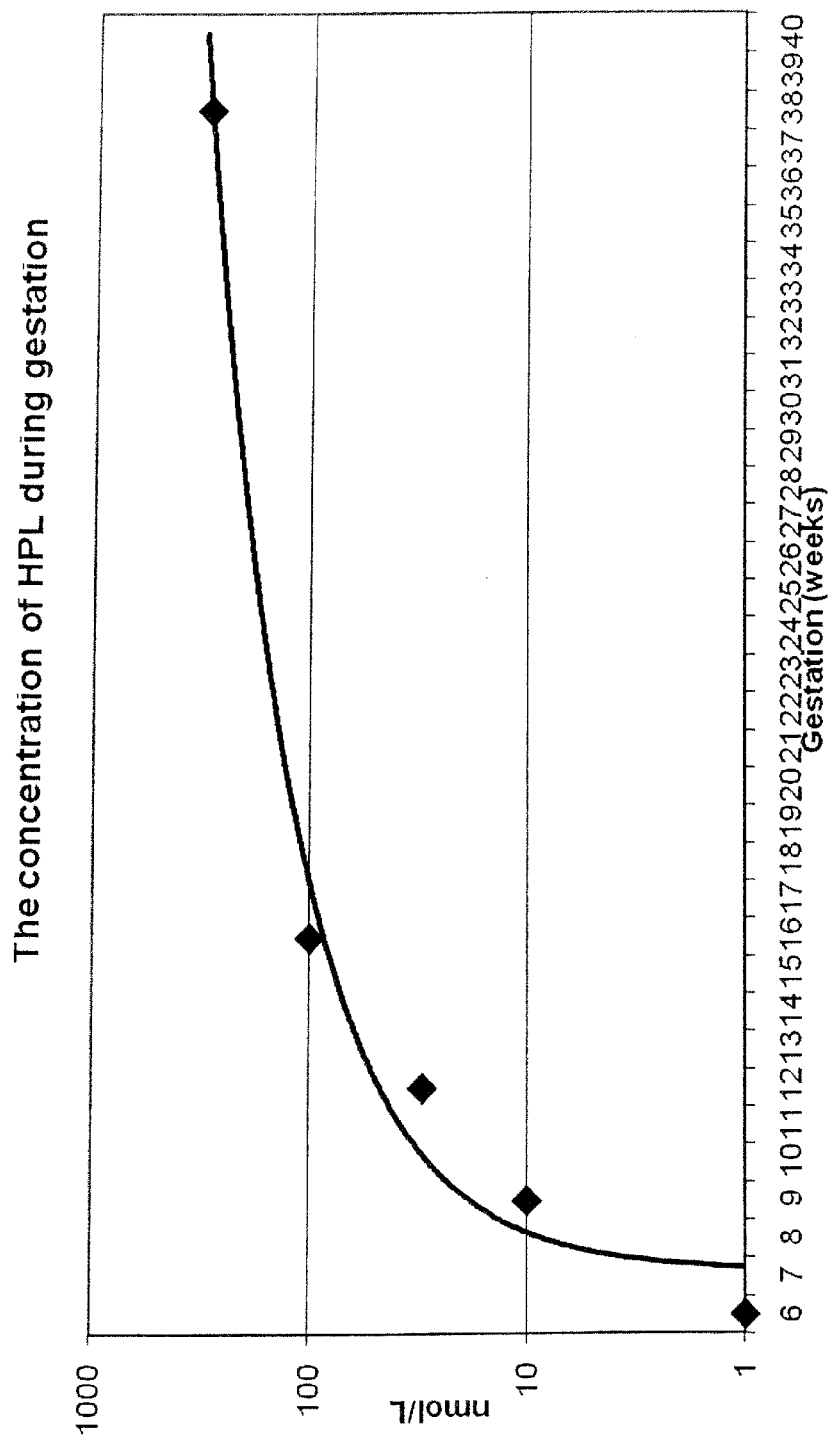
FIG. 1 shows the secretion profile of hPL in nmol/L as a function of weeks of pregnancy.

Interestingly, there is correlation between the mass of the placenta and the amount of hPL present and it is hypothesised that each trophblastic cell synthesizes a fixed amount of the hPL per day and as the number of cells increases so too does the amount of hPL synthesised and secreted. For this reason hPL has been suggested as a useful marker for detecting certain abnormalities during pregnancy, especially in the period 30-35 weeks, in the third trimester of pregnancy. Only very low levels of the hPL are secreted before 6 weeks. After 6 weeks the amount secreted increases exponentially until about week 24 when the concentration curve starts to flatten out (see FIG. 1).

Stage of pregnancy as employed herein is intended to refer to associating a time point with the pregnancy, for example the number of weeks of gestation, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 weeks or ranges thereof. It is not simply intended to refer to providing a binary result i.e. a positive or negative result, pregnant or not pregnant.

Quantifying the amount of hPL or other hormone referred to herein may be the absolute quantity, in mass per unit volume, moles (nano moles etc) per unit volume or as international units per unit volume, it also includes establishing the relative amount, for example by reference to a standard. In one embodiment the method employed is semi-quantitative.

Fragment thereof as employed herein refers to a detectable fragment that corresponds to the actual amount of hPL present, and may include a subunit such as the α-subunit.

In one embodiment the method may be able to distinguish the following time points in a pregnancy: 6 weeks or less, 6 to 9 weeks, 10 to 12 weeks, 13 to 15 weeks, 16 to 18 weeks, 19 to 21 weeks, and/or 21 to 24 weeks.

The stages less than 6 weeks may be characterised by a hPL concentration of 2 nmol/L or less. The stage 6 weeks to up to 9 weeks may be characterised by a concentration in the range above 2 nmol/L up to about 9 nmol/L. The stage 10 to 12 weeks may be characterised by a concentration in the range above 9 nmol/L to about 34 nmol/L. The stage 13 to 15 weeks may be characterised by a concentration in the range above 80 nmol/L to about 95 nmol/L. The stage 16 to 18 weeks may be characterised by a concentration in the range above 95 nmol/L to about 105 nmol/L. The stage 19 to 21 weeks may be characterised by a concentration in the range above 105 nmol/L to about 200 nmol/L. The stage 22 weeks to 24 weeks may be characterised by a concentration in the range above 200 nmol/L to about 225 nmol/L.

In one embodiment the method may distinguish between the following stages of pregnancy: 6 weeks and less, 7/8 weeks, 9 weeks, 10/11 weeks, 11/12 weeks, 12/13 weeks, 14/15/16 weeks, 17/18 weeks, 18/19 weeks, 19/20 weeks, 21 weeks, 22 weeks, 23 weeks, and/or 24 weeks and above.

A hPL concentration of 0.04 mg/L or below may be indicative of a pregnancy in the period 6 weeks or less. A hPL concentration in the range 0.04-0.05 mg/L may be indicative of a 7/8 week pregnancy. A hPL concentration in the range 0.1 to 0.2 mg/L may be indicative of a 9 week pregnancy. A hPL concentration in the range 0.25 to 0.35 mg/L may be indicative of a 10/11 week pregnancy. A hPL concentration in the range 0.3 to 0.5 mg/L may be indicative of a 11/12 week pregnancy. A hPL concentration in the range 0.65 to 0.7 mg/L may be indicative of a 12/13 week pregnancy. A hPL concentration of about 0.9 mg/L may be indicative a 14/15/16 week pregnancy. A hPL concentration of about 1.5 mg/L may be indicative of a 17/18 week pregnancy. A hPL concentration in of about 2.5 mg/L may be indicative of a 19/20 week pregnancy.

The above identified figures are based on the amounts of hPL in serum. Whilst hPL has a short half life in serum it seems that due to the size of the peptide, at least some hPL is filtered at the glomerulus into the urine. Once in the urine hPL seems to be protected from degradation or further degradation. Thus the profile of secretion of hPL in urine seems to follows the same curve as that observed in serum, even though the absolute quantities of hPL in urine are lower than those observed in serum. However, sensitive analytical techniques such as ELISA assays are able to detect and quantify the amounts of hPL in urine, which over a 24 hour period, at about week 8 of pregnancy is approximately 10 µg.

The method herein may be applied to determining the stage of pregnancy over 24 weeks. The amounts of hPL in serum towards the end of the pregnancy may reach level approaching 5-7 mg/L.

At least the amounts of hPL shown in Table 1 have been identified in urine:

TABLE 1

| Gestation (weeks) | Gestation (days) | Level (micrograms) |
| --- | --- | --- |
| 8 | 56 | 10 |
| 14 | 98 | 13.1 |
| 14.4 | 101 | 17.7 |
| 19.2 | 135 | 56.9 |
| 24.3 | 170 | 59.5 |

TABLE 1-continued

| Gestation (weeks) | Gestation (days) | Level (micrograms) |
| --- | --- | --- |
| 25.4 | 178 | 31.1 |
| 28.2 | 198 | 100.4 |
| 29 | 203 | 69.2 |
| 31.7 | 222 | 76.4 |
| 31.9 | 223 | 36.5 |
| 31.9 | 223 | 121.5 |
| 34.1 | 239 | 93.2 |
| 36.6 | 256 | 105 |

The absolute amounts of hPL detected and/or extracted from the sample depends on the exact techniques employed. The more sensitive the technique the higher the value the may ultimately be detected. Thus the levels in Table 1, may be higher depending on which technique is employed.

The present disclosure is particularly suitable for establishing the stage of pregnancy when the female is in the first or second trimester of pregnancy.

In one embodiment the method is suitable for distinguishing one gestation week from another, in particular where the weeks fall within the range 7 to 28 weeks.

Methods for establishing the stage of pregnancy based on a hormone (analyte) and algorithms which may be adapted for use in the present disclosure are described in WO 2006/100415 (see in particular page 11 to page 16).

It is very convenient to be able to establish the stage of a pregnancy based on the lateral flow technology employing urine as a sample. Therefore the technology described herein is likely to have broad application, which can be readily implemented by those skilled in the relevant technical field.

The above test may of course be performed after performing a test based on hCG levels which has identified the woman as pregnant. This may be important for an unconfirmed pregnancy at an early stage because a test based only on hPL before 6 weeks alone is not able to confirm the pregnancy. Thus in one embodiment a device testing for hPL concentrations is provided in a kit with a separate device testing for hCG levels, for example CLEARBLUE EASY®.

In one embodiment in the method according to the present disclosure a combination of hormone levels are measured, for example, the concentration of hPL and hCG are measured, for example concomitantly or sequentially, such as in the same device (or alternatively in separate devices). This is particularly useful when the pregnancy is at a stage of six weeks or less because it enables the stage of the pregnancy to be established as 1 to 2 weeks, 2 to 3 weeks or 3 to 6 weeks, in addition the stages identifiable employing hPL alone.

This, may for example be achieved by employing a single device comprising multiple, such as 2, 3 or 4 separate assay strips.

Alternatively, or in addition the method may also test for concentrations of relaxin. Like hCG this hormone is secreted from very shortly after implantation and therefore relaxin and hPL may be used in combination to ascertain the stage of pregnancies, for example upto and including the 6 weeks stage, in addition the stages identifiable employing hPL alone.

In one embodiment relaxin is used in an assay for testing if a sample indicates that the relevant female, from which it was derived, is pregnant and a subsequent test is performed to determine the hPL levels to establish the stage of the pregnancy.

The levels of relaxin are at the highest levels around week 10 to 12. Thus in combination with at least hPL and optionally other hormones, for example those described herein, relaxin may be particularly useful in distinguishing pregnancies at the 10 to 12 week stage.

Levels of unconjugated estradiol become significant by about week 13 of pregnancy and may be used in combination with at least hPL and optionally other hormones, especially those described herein, to identify the relevant stage of the pregnancy. The combination of estradiol and hPL may be particularly useful for, in particular, distinguishing pregnancies at the 13 week stage.

Further hormones that may be analysed in a method/device according to the present disclosure include luteinizing hormone and/or follicle stimulating hormone.

In one embodiment the method herein is suitable for identifying a stage of pregnancy in the range 6 to 28 weeks, for example 7 to 24 weeks such as 8, 9, 10, 11, 12, 13, 14, 15, 16, 17, 18, 19, 20, 21, 22 or 23 weeks or combinations thereof.

In an alternative embodiment, for example involving analysis of at least two hormones (analytes) a stage of pregnancy can be identified in the range 1-2, 2-3, 3-6 weeks, wherein the remaining stages are identifiable as per any one of the embodiments described herein.

Methods of measuring hormone levels include protein array, HPLC (high performance liquid chromatograph), SDS-Page, Western blotting, and immunoassays. There are different forms of immunoassays, for example employing enzymes and/or fluorescence. One particularly sensitive form of immunoassay is an ELISA assays (enzyme linked immunosorbent assay), sometimes referred to as a sandwich assay. The fact that the test employs two distinct antibodies directed to the same target, increases the accuracy/specificity of the test.

Examples of suitable technology which may be adapted to implement the present disclosure are described in EP 0219194, see in particular page line 14-23, which describes test strips, page 2 lines 27-36 which describes a typical device, page 2 lines 37-55 which describes the porous solid phase further and "sandwich" and competition assays, page 3 lines 34-39 discusses suitable properties of the porous carrier, such as nitrocellulose, in the context of allowing movement of the labels/particles. The latter text also discusses suitable labels will generally be in the size range 0.05 to 0.5 microns.

Suitable labels also include coloured particles of material, for example gold sol, dye sol or a coloured polymer such as laytex, which accumulates to provide a signal/result, in particular in a detection zone. See for example EP 0219194 page 5 lines 2-15, the preparation of Gold sol, Dye Sol, and Coloured Particles on page 12, and the coupling of an antibody to one of the said labels is described on page 13 lines 10-19 thereof.

Alternatively, for tests performed by professionals then the label on the antibody, for example employed in the immunoassay may be a radiolabel.

Alternatively the levels of hPL can be established indirectly employing for example QPCR to measure the levels of mRNA in a blood sample.

In one embodiment the sample is blood, serum or plasma.

In one embodiment the sample is a urine sample.

Generally the method, test and/or device should have a sensitivity of 50 IU/L (international units per Liter) such as 10, 15, 20, 25, 30, 35, 40 or 45 IU/L.

The principles of an ELISA assay are simple in that an antibody specific to the target molecule is fixed to an insoluble bead (which may be coloured) or surface. The test sample is then introduced and if target molecules are present the antibody binds them. Finally, a second distinct antibody, which is labelled such that is can be detected, is introduced (or may have been present in the test pot) and binds the target molecule in a different location to the first antibody thereby forming a sandwich of the target. Alternatively the second antibody may be directed to the first antibody. Once bound a label is activated and can be detected, measured and quantified, if so desired.

In one embodiment the device is a lateral flow device comprising a liquid transport means, for example a porous carrier such as nitrocellulose.

Figure 2:
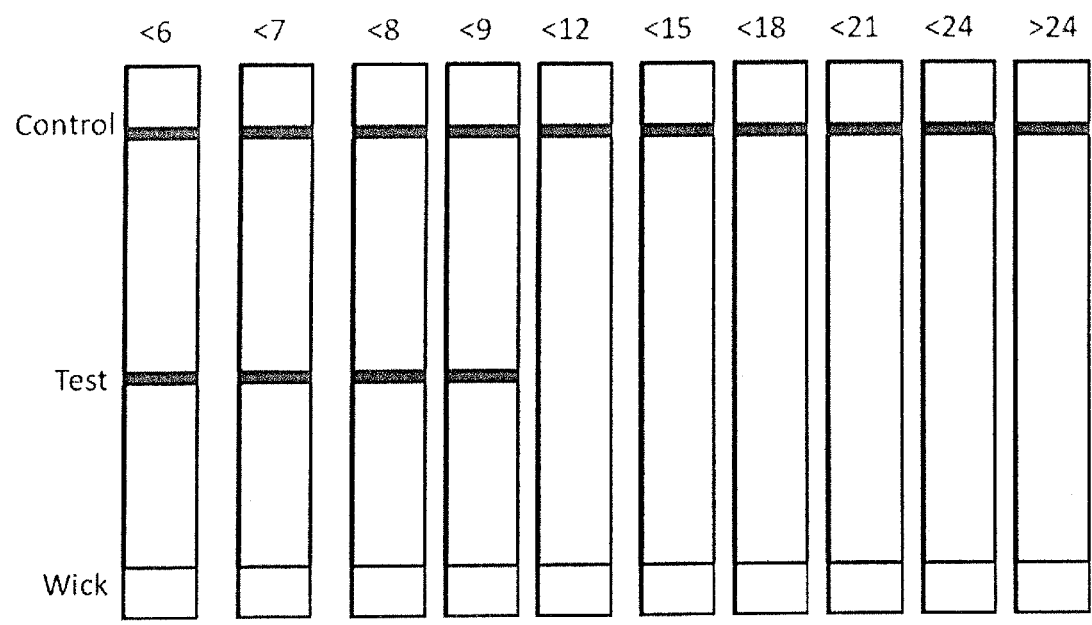
FIG. 2 shows a simple embodiment of a test arrangement suitable for indicating the stage of a pregnancy.

In some simple tests such as first generation pregnancy tests a positive result was simply a blue line that appeared in the test window. In a simple embodiment of the present disclosure test strips comprising the required reagents may be provided in the form of time points and labelled with the relevant stage of pregnancy as shown in FIG. 2. This uses technology as described in EP 291194 and quantification techniques described in WO 2006/100415. The readout from such as test is quite simple. Therefore, in one embodiment the device comprises multiple results windows, for example wherein each result window is labelled with a time point so the user can readily read the result therefrom and establish the stage without any interpretation. The accumulation of coloured beads in the relevant window or windows may indicate the result.

Figure 4A:
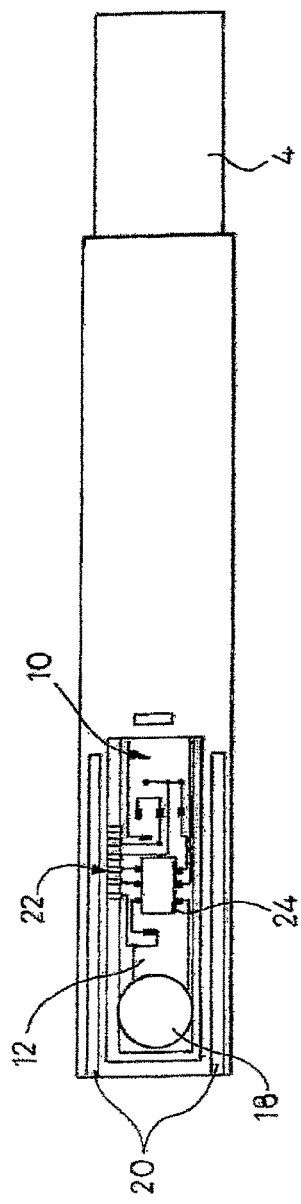
FIGS. 4A and 4B show cutaway plan and side views respectively of the device in FIGS. 3A and 3B.
Figure 4B:
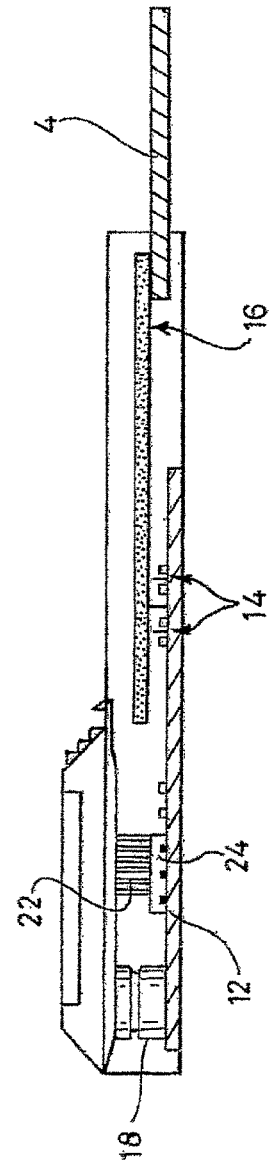

However, optical density readings may be taken on digital devices either in the laboratory or in handheld disposable devices, for example as described in WO 2007/017648. In one embodiment of the present disclosure there the device is as shown in FIG. 3 or 4 below, namely a device approximately 12 cm in length and 2 cm. The device comprises a housing (2), for example formed from an opaque plastic material. At one end of the housing there is provided a narrow opening through which a liquid transport or carrier can protrude beyond the housing for contacting with a sample liquid.

A display (6) for displaying information to the user is releasably attached to the device, such that it can be removed from the device after generation of an assay result. Downward pressure on the resiliently deformable clip (8) facilitates said removal. The display is such that the result and any other information thereon, can be retained after removal of the display from the device, for future reference.

The device housing comprises an analytical assembly labelled (10), which comprises as circuit board (12) supporting two LEDs and two photodiodes (14), aligned with a test zone of a nitrocellulose strip lateral flow strip (16) which is in liquid flow communication with the sampling portion (4) of the liquid transport or carrier. The test zone is the zone in which a labelled reagent accumulates in the presence (or absence, as appropriate) of the analyte of interest. This accumulation affects the optical property of the test strip (16), such as its reflectivity or transmissivity, a property that can be measured by the LED/photodiode arrangement. The arrangement produces an output current, the magnitude of which is related to the amount of label accumulated in the test zone.

The analytical assembly (10) also comprises an electrical power source (button cells 18) to provide power to the display (6) when it is attached to the housing (2).

Grooves (20) are provided on the top of the housing to accommodate a slight flanged portion of the display (6). The display (6) is retained in the housing in a suitably shaped and dimensioned aperture by clip (8). When correctly positioned, electrical connectors on the display come into contact with electrical connectors (22) provided on the housing, thereby ensuring electrical connections between the display (6) and the analytical assembly (10).

The analytical member (10) comprises signal transduction components (24), comprising a data storage buffer, an analogue to digital converter (ADC) and a microprocessor or microcontroller. The display (6) is responsive to an output from the microprocessor or microcontroller.

Flow sensing for determining assay results is described in US patent application publication No: 2005/037511. Assay devices and methods are taught in US application application publication No: 2008/213875.

In one embodiment the disclosure provides a device adapted to establish the approximate stage of a pregnancy from the concentration of at least hPL in a sample, for example comprising one or more elements described herein. The device may optionally provide a positive or negative result, in relation to pregnancy, for example based on hCG. In this embodiment a device employed may comprise reagents for the analysis of hPL and hCG.

Advantageously, the analysis can be repeated at different time points to provide evidence that the pregnancy is progressing and the foetus is growing.

In one embodiment the result is displayed as a number or range in a window, for example in the form of a digital display.

In one embodiment the device is a handle held device, for example a disposable hand held device.

In one aspect the device comprises an anti human placental lactogen antibody, for example a monoclonal antibody. The antibody may optionally be labelled, for example as discussed above.

In one embodiment the device comprises a further distinct placental lactogen antibody, for example monoclonal antibody, wherein said further antibody is labelled to allow detection of binding to hPL or a relevant fragment thereof.

Alternatively a second antibody employed may be anti-antibody antibody and for example may be directed at the Fc region of the first antibody. This second antibody may be labelled.

Where a first and second antibody is employed then each antibody may be labelled.

An anti human placental lactogen antibody as employed herein is intended to refer to an antibody specific to said antigen (hPL).

In one embodiment a combination of antibodies, for example monoclonal antibodies in admixture are employed, directed to the specific hormones to be tested.

In one embodiment an antibody employed has a fluorescent label. In one embodiment a further antibody, for example to a distinct hormone, is employed with a fluorescent label that emits light a wavelength distinct from the first fluorescently labelled antibody.

If the device is for sale to the public, for example over the counter in pharmacies and supermarkets, then the assay therein should be robust enough to handle an appropriate range of concentration of relevant hormones, likely to be encountered and provide a result for the end user.

It may be advisable for testing to be performed on the first urine sample of day which is passed by the female. Therefore in one embodiment the device is accompanied by instructions explaining the latter.

Having said this, if the device is to be supplied to hospitals and doctors it may be important to know very accurately if the pregnancy is less than 9 weeks, less than 12 weeks, less than 18 weeks, 21 weeks and/or 24 weeks. In this instance the test, kit, device and/or reagent may be provided as separately optimised entities for each relevant time point.

The optimisation may involve modifying the concentration of reagents employed and/or the combination of hormones employed.

In a further embodiment the method employed herein may be adapted to detect a decrease in hPL levels in a female, as a means of monitoring the loss or termination of the foetus. The adequate monitoring of the latter can be problematic for medical professionals. A routine test for identifying the decrease in the levels of hPL would therefore be very useful.

In one embodiment the disclosure provides use of an anti hPL antibody such as monoclonal antibody, for example a murine, porcine, ovine, bovine, goat, camel, rat, rabbit or other antibody, for use in the quantification of the hPL in a fluid sample, such as a blood, serum, plasma or urine sample, derived from a human female, for example for the purpose of estimating the stage of pregnancy.

In one or more embodiments of the disclosure the antibody employed is directed to the α-subunit of hPL.

A number of monoclonal antibodies are commercially available for example:

Mouse Anti-Human placental lactogen (epitope 2) Monoclonal Antibody, Unconjugated, Clone INN-hPL-37 from Abcam, Mouse Anti-Human PLACENTAL LACTOGEN Monoclonal Antibody, Unconjugated, Clone INN-hPL-5 from AbD Serotec, and Mouse Anti-Placental Lactogen (hPL) Monoclonal Antibody, Unconjugated, Clone LIP-603 from Acris Antibodies GmbH.

Alternatively, antibodies including monoclonal antibodies can be readily prepared by routine techniques in the relevant technical field, for example by immunizing a host with hPL conjugated to a suitable carrier such as ovalbumin or the like. The antibody employed should be specific to hPL, for example having a cross-reactivity of 1% or less or as appropriate in the circumstances.

In one embodiment the disclosure provides a kit comprising a device and/or reagent for testing the concentration hPL in a fluid body sample, derived from a human female, for the purpose of establishing the stage of pregnancy.

In one embodiment there is a provided a kit adapted for identifying a drop in hPL levels after loss or termination of a foetus.

Given that the test described herein relies on the correlation between placenta mass and the concentration of the secretion of hPL then if the female is impregnated with two or more foetuses then the present method may present the result as a later stage of pregnancy than is appropriate. Having said this, it would seem that multiple impregnation accounts for only 3% of pregnancies and therefore, the test/method/device and uses of the present disclosure represent a practical step forward in providing information to individuals in a convenient, cost effective and efficient manner.

It is envisaged that one or more embodiments described herein may be combined, as technically appropriate.

In the context of this specification "comprising" is to be interpreted as "including".

Aspects of the disclosure comprising certain elements are also intended to extend to alternative embodiments "consisting" or "consisting essentially" of the relevant elements.

All documents referred to herein are incorporated by reference in their entirety.

EXAMPLES

Figure 5:
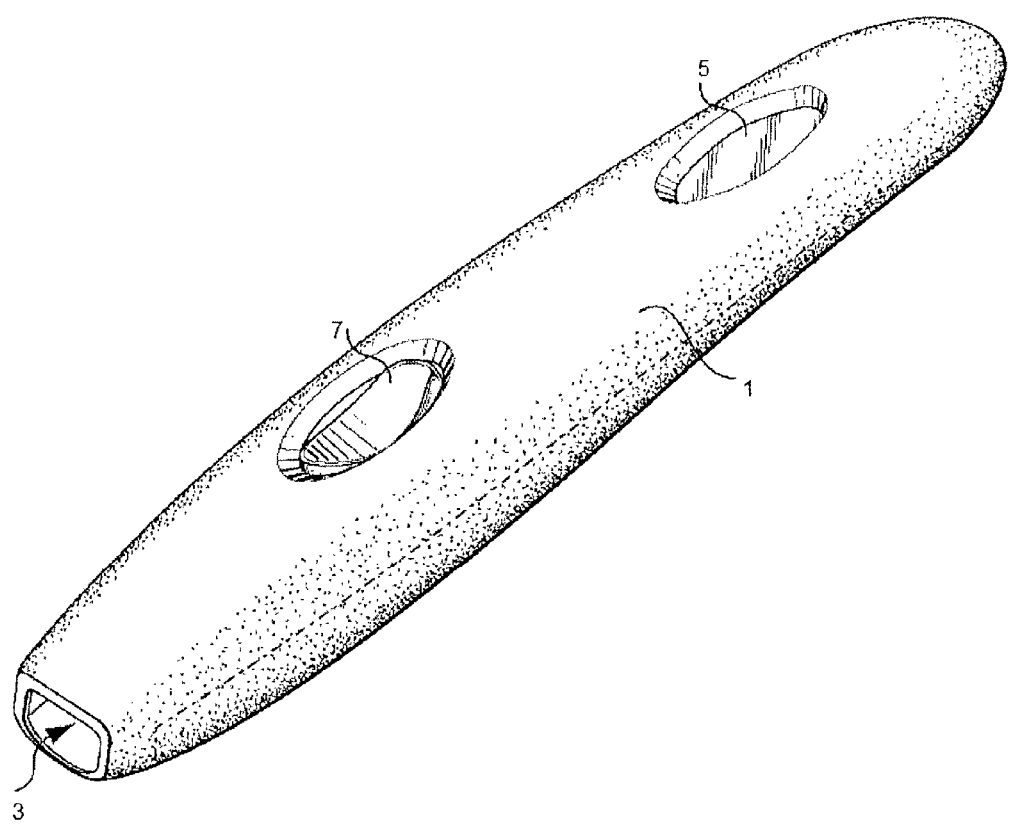
FIG. 5 shows an arrangement of a result reading device.

An embodiment of an assay result reading device having both "shared" photodetectors and "commonly read" zones is illustrated in FIG. 5. The reading device is about 12 cm long and about 2 cm wide and is generally finger or cigar-shaped.

In preferred embodiments, the housing is no larger than about 12 cm long, about 2.5 cm wide, and about 2.2 cm tall. However, any convenient shape may be employed, such as a credit card shaped reader. The device comprises a housing 1 formed from a light-impermeable synthetic plastics material (e.g. polycarbonate, ABS, polystyrene, high density polyethylene, or polypropylene or polystyrol containing an appropriate light-blocking pigment, such as carbon). At one end of the reading device is a narrow slot or aperture 3 by which a test strip (not shown) can be inserted into the reader. On its upper face the reader has two oval-shaped apertures. One aperture accommodates the screen of a liquid crystal display 5 which displays information to a user e.g. the results of an assay, in qualitative or quantitative terms. The other aperture accommodates an eject mechanism actuator 7 (in the form of a depressible button), which when actuated, forcibly ejects an inserted assay device from the assay reading device.

The test strip for use with the reading device is a generally conventional lateral flow test stick e.g. of the sort disclosed in U.S. Pat. No. 6,156,271, U.S. Pat. No. 5,504,013, EP 728309, or EP 782707. The test strip and a surface or surfaces of the slot in the reader, into which the test strip is inserted, are so shaped and dimensioned that the test strip can only be successfully inserted into the reader in the appropriate orientation. The assay device and a surface or surfaces of the slot in the reader, into which the assay device is inserted, may also be so shaped and dimensioned that there is a precise three dimensional alignment of the reader and an inserted assay device, which ensures that the assay result can be read correctly the reader. When a test strip is correctly inserted into the reader, a switch is closed which activates the reader from a "dormant" mode, which is the normal state adopted by the reader, thereby reducing energy consumption.

Enclosed within the housing of the reader (and therefore not visible in FIG. 5) are a number of further components, including a reader comprising three LED's. When a test strip is inserted into the reader, each LED is aligned with a respective zone of the test strip. The first LED is aligned with the test zone, the second LED is aligned with the reference zone and the third LED is aligned with the control zone. Two photodiodes detect light reflected from the various zones and generate a current, the magnitude of which is proportional to the amount of light incident upon the photodiodes. The current is converted into a voltage, buffered by buffer and fed into an analogue to digital converter (ADC). The resulting digital signal is read by microcontroller.

In some embodiments, a separate photodiode is provided to detect from each zone (i.e. the number of photodiodes equals the number of zones from which reflected light measurements are made).

In other embodiments, the number of photodetectors is less than the number of zones. One photodiode detects light reflected from the test zone and some of the light reflected from the reference zone. The other photodiode detects some of the light reflected from the reference zone and the light reflected from the control zone. The microcontroller switches on the LED's one at a time, so that only one of the three zones is illuminated at any given time-in this way the signals generated by light reflected from the respective zones can be discriminated on a temporal basis.

A switch which is closed by insertion of an assay device into the reader, and which activates the microcontroller. The device further comprises a power source (typically a button cell or two button cells), and an LCD device responsive to output from the microcontroller.

In use, a dry test strip (i.e. prior to contacting the sample) is inserted into the reader, this closes the switch activating the reader device, which then performs an initial calibration. The intensity of light output from different LED's is rarely identical. Similarly, the photodetectors are unlikely to have identical sensitivities. Because such variation could affect the assay reading an initial calibration is effected, in which the microcontroller adjusts the length of time that each of the three LED's is illuminated, so that the measured signal from each of the three zones (test, reference and control) is approximately equal and at a suitable operating position in a linear region of the response profile of the system (such that a change in intensity of light reflected from the various zones produces a directly proportional change in signal).

After performing the initial calibration, the device performs a further, finer calibration. This involves taking a measurement ("calibration value") of reflected light intensity for each zone whilst the test strip is dry-subsequent measurements ("test values") are normalized by reference to the calibration value for the respective zones (i.e. normalized value=test value/calibration value).

To conduct an assay, a sample receiving portion of the test strip is contacted with the liquid sample. In this case of a urine sample for instance, the sample receiving portion may be held in a urine stream, or a urine sample collected in a receptacle and the sample receiving portion briefly (about 5-10 seconds) immersed in the sample. Sampling may be performed whilst the test strip is inserted in the reader or, less preferably, the strip can be briefly removed from the reader for sampling and then reintroduced into the reader. Measurements of reflected light intensity from one or more (preferably all three) of the zones are then commenced, typically after a specific timed interval following insertion of the test strip into the reader. Desirably the measurements are taken at regular intervals (e.g. at between 1-10 second intervals, preferably at between 1-5 second intervals). The measurements are made as a sequence of many readings over short (10 milliseconds or less) periods of time, interleaved zone by zone, thereby minimising any effects due to variation of ambient light intensity which may penetrate into the interior of the reader housing.

REFERENCES

Sorenson et al (1995) Human reproduction 10: 453-458
Kaplan et al (1965) Science 147: 751
Josimovich et al (1964) Am J. Obst & Gynec 88:867-879

```
                                                              SEQ ID NO: 1
            10         20         30         40         50         60
    MAPGSRTSLL LAFALLCLPW LQEAGAVQTV PLSRLFDHAM LQAHRAHQLA IDTYQEFEET 70         80         90        100        110        120
    YIPKDQKYSF LHDSQTSFCF SDSIPTPSNM EETQQKSNLE LLRISLLLIE SWLEPVRFLR 130        140        150        160        170        180
    SMFANNLVYD TSDSDDYHLL KDLEEGIQTL MGRLEDGSRR TGQILKQTYS KFDTNSHNHD 190        200        210
    ALLKNYGLLY CFRKDMDKVE TFLRTVQCRS VEGSCGF
```

The invention claimed is:

1. A disposable immunoassay device-comprising:
a housing comprising:
  a) a test strip comprising:
    a sampling portion;
    a test zone in fluid communication with the sampling portion, the test zone comprising at least one anti-hPL antibodies or antigen binding fragments thereof; the at least one anti-hPL antibodies is immobilized in the test zone;
    the test zone further comprising at least one labeled anti-hPL antibodies or antigen binding fragments thereof wherein the label comprises a colored label or a fluorescent label,
  b. an electrical power source,
  c. a detector aligned with the test zone for detecting a property of the test zone which is affected by the colored label or the fluorescent label and producing a signal having a magnitude which is proportional to an amount of the colored label or the fluorescent label in the test zone, thereby quantifying the hormone analyte in a urine sample; and
  d. a display providing information related to the stage of pregnancy as a number of a given week selected from the group consisting of 8, 9, 10, 11, 12, 13, 14, 15, 16, 17.18, 19, 20, 21, 22, 23 and 24, or range of weeks,
  wherein the range is selected from 8 to 24 weeks, wherein the number displayed is correlated to the signal produced by the detector.

2. The disposable immunoassay device of claim 1, wherein the display is releasably attachable from the remainder of the device.

3. The disposable immunoassay device of claim 1, wherein display is digital.

4. The disposable immunoassay device of claim 1, wherein the test strip is a lateral flow strip.

5. The disposable immunoassay device of claim 4, wherein the lateral flow strip is a nitrocellulose lateral flow strip.

6. The disposable immunoassay device of claim 1, wherein the device is a hand-held device.

7. The disposable immunoassay device of claim 1, wherein said at least one of anti-hPL antibodies and binding fragments thereof is monoclonal.

8. The disposable immunoassay device according to claim 1, wherein the label comprises particles or heads.

* * * * *

SEQUENCE LISTING

<160> NUMBER OF SEQ ID NOS: 1

<210> SEQ ID NO 1
<211> LENGTH: 217
<212> TYPE: PRT
<213> ORGANISM: Homo sapiens

<400> SEQUENCE: 1

Met Ala Pro Gly Ser Arg Thr Ser Leu Leu Leu Ala Phe Ala Leu Leu
1               5                   10                  15

Cys Leu Pro Trp Leu Gln Glu Ala Gly Ala Val Gln Thr Val Pro Leu
            20                  25                  30

Ser Arg Leu Phe Asp His Ala Met Leu Gln Ala His Arg Ala His Gln
                35                  40                  45

Leu Ala Ile Asp Thr Tyr Gln Glu Phe Glu Glu Thr Tyr Ile Pro Lys
        50                  55                  60

Asp Gln Lys Tyr Ser Phe Leu His Asp Ser Gln Thr Ser Phe Cys Phe
65                  70                  75                  80

Ser Asp Ser Ile Pro Thr Pro Ser Asn Met Glu Glu Thr Gln Gln Lys
                85                  90                  95

Ser Asn Leu Glu Leu Leu Arg Ile Ser Leu Leu Leu Ile Glu Ser Trp
            100                 105                 110

Leu Glu Pro Val Arg Phe Leu Arg Ser Met Phe Ala Asn Asn Leu Val
        115                 120                 125

Tyr Asp Thr Ser Asp Ser Asp Tyr His Leu Leu Lys Asp Leu Glu
    130                 135                 140

Glu Gly Ile Gln Thr Leu Met Gly Arg Leu Glu Asp Gly Ser Arg Arg
145                 150                 155                 160

Thr Gly Gln Ile Leu Lys Gln Thr Tyr Ser Lys Phe Asp Thr Asn Ser
                165                 170                 175

His Asn His Asp Ala Leu Leu Lys Asn Tyr Gly Leu Leu Tyr Cys Phe
            180                 185                 190

Arg Lys Asp Met Asp Lys Val Glu Thr Phe Leu Arg Thr Val Gln Cys
        195                 200                 205

Arg Ser Val Glu Gly Ser Cys Gly Phe
    210                 215